US011950923B2

United States Patent
Schuler et al.

(10) Patent No.: US 11,950,923 B2
(45) Date of Patent: *Apr. 9, 2024

(54) SYSTEMS, METHODS AND APPARATUSES FOR PROVIDING BIOELECTRONIC NEUROCODE-BASED THERAPIES TO MAMMALS

(71) Applicant: ELECTROCEUTICALS, LLC, Albuquerque, NM (US)

(72) Inventors: Eleanor Schuler, Albuquerque, NM (US); Luis M. Ortiz, Albuquerque, NM (US); Kermit D. Lopez, Albuquerque, NM (US)

(73) Assignee: Electroceuticals, LLC, Albuquerque, NM (US)

( * ) Notice: Subject to any disclaimer, the term of this patent is extended or adjusted under 35 U.S.C. 154(b) by 306 days.

This patent is subject to a terminal disclaimer.

(21) Appl. No.: 17/387,286

(22) Filed: Jul. 28, 2021

(65) Prior Publication Data
US 2021/0353223 A1 Nov. 18, 2021

Related U.S. Application Data

(63) Continuation of application No. 15/179,113, filed on Jun. 10, 2016, now Pat. No. 11,154,238.
(Continued)

(51) Int. Cl.
*A61B 5/00* (2006.01)
*A01K 29/00* (2006.01)
(Continued)

(52) U.S. Cl.
CPC .......... *A61B 5/4836* (2013.01); *A01K 29/005* (2013.01); *A61B 5/0002* (2013.01);
(Continued)

(58) Field of Classification Search
CPC ............ A01K 29/005; A61B 2503/40; A61B 5/0002; A61B 5/076; A61B 5/4836; G16H 40/67; H04L 67/12
See application file for complete search history.

(56) References Cited

U.S. PATENT DOCUMENTS

| 4,852,573 A | 8/1989 | Kennedy |
| 5,188,104 A | 2/1993 | Wernicke et al. |

(Continued)

FOREIGN PATENT DOCUMENTS

| EP | 0569522 B1 | 6/1999 |
| WO | 02/04068 A1 | 1/2002 |

OTHER PUBLICATIONS

U.S. Appl. No. 12/233,4212, filed Dec. 12, 2008, Schuler et al.
(Continued)

*Primary Examiner* — George Manuel
(74) *Attorney, Agent, or Firm* — Ortiz & Lopez, PLLC; Kermit D. Lopez; Luis M. Ortiz

(57) ABSTRACT

Systems, methods, and apparatuses monitor mammal conditions, report condition changes, and provide neurocode-based treatment in response to condition changes. A mammal implantable controller includes modules to monitor, wirelessly communicate to external computers, and administer treatment received from a remote computer based on monitoring of changes in mammal condition as analyzed by the remote computer. External computers can be provided in the form of a mobile device (e.g., smartphone/tablet), resident treatment pods, and treatment servers. Treatment can be provided to change biological function or trigger cell death in cancer cells.

11 Claims, 10 Drawing Sheets

Related U.S. Application Data

(60) Provisional application No. 62/202,286, filed on Aug. 7, 2015.

(51) Int. Cl.
*A61B 5/07* (2006.01)
*G16H 40/67* (2018.01)
*H04L 67/12* (2022.01)

(52) U.S. Cl.
CPC ............ *A61B 5/076* (2013.01); *G16H 40/67* (2018.01); *H04L 67/12* (2013.01); *A61B 2503/40* (2013.01)

(56) References Cited

U.S. PATENT DOCUMENTS

| | | | |
|---|---|---|---|
| 5,231,988 A | 8/1993 | Wernicke et al. | |
| 5,263,480 A | 11/1993 | Wernicke et al. | |
| 5,527,586 A | 6/1996 | Schuler et al. | |
| 5,540,730 A | 7/1996 | Terry, Jr. et al. | |
| 5,610,136 A | 3/1997 | McMichael | |
| 6,171,239 B1 | 1/2001 | Humphrey | |
| 6,522,926 B1 | 2/2003 | Kieval et al. | |
| 6,575,969 B1 | 6/2003 | Ritiman, III et al. | |
| 6,587,719 B1 | 7/2003 | Barrett et al. | |
| 6,633,779 B1 | 10/2003 | Schuler et al. | |
| 6,681,136 B2 | 1/2004 | Schuler et al. | |
| 6,751,501 B1 | 6/2004 | Schuler et al. | |
| 6,775,573 B2 | 8/2004 | Schuler et al. | |
| 6,826,428 B1 | 11/2004 | Chen et al. | |
| 6,832,114 B1 | 12/2004 | Whitehurst et al. | |
| 6,851,145 B2 | 2/2005 | Smith et al. | |
| 6,853,862 B1 | 2/2005 | Marchal et al. | |
| 6,937,903 B2 | 8/2005 | Schuler et al. | |
| 6,941,171 B2 | 9/2005 | Mann et al. | |
| 6,957,106 B2 | 10/2005 | Schuler et al. | |
| 7,010,356 B2 | 3/2006 | Jog et al. | |
| 7,011,638 B2 | 3/2006 | Schuler et al. | |
| 7,058,446 B2 | 6/2006 | Schuler et al. | |
| 7,062,324 B2 | 6/2006 | Schuler et al. | |
| 7,146,210 B2 | 12/2006 | Palti | |
| 7,160,239 B2 | 1/2007 | Ichikawa et al. | |
| 7,308,302 B1 | 12/2007 | Schuler et al. | |
| 7,316,913 B2 | 1/2008 | Gerdes et al. | |
| 7,725,176 B2 | 5/2010 | Schuler et al. | |
| 8,315,712 B2 | 11/2012 | Schuler et al. | |
| 8,467,869 B2 | 6/2013 | Schuler | |
| 8,478,398 B2 | 7/2013 | Schuler | |
| 8,509,887 B2 | 8/2013 | Schuler et al. | |
| 8,656,930 B2 | 2/2014 | Schuler et al. | |
| 8,725,246 B2 | 5/2014 | Schuler | |
| 8,781,593 B2 | 7/2014 | Schuler | |
| 8,818,502 B2 | 8/2014 | Schuler | |
| 8,831,738 B2 | 9/2014 | Schuler et al. | |
| 9,031,537 B2 | 5/2015 | Ortiz et al. | |
| 9,032,964 B2 | 5/2015 | Schuler et al. | |
| 9,254,388 B2 | 2/2016 | Schuler | |
| 9,295,835 B2 | 3/2016 | Schuler | |
| 2001/0051766 A1 | 12/2001 | Gazdinski | |
| 2002/0010491 A1 | 1/2002 | Schoenbach et al. | |
| 2002/0010499 A1 | 1/2002 | Rigaux et al. | |
| 2002/0049482 A1 | 4/2002 | Fabian et al. | |
| 2003/0045909 A1 | 3/2003 | Gross et al. | |
| 2003/0055467 A1 | 3/2003 | Ben-Haim et al. | |
| 2003/0170898 A1 | 9/2003 | Gundersen et al. | |
| 2003/0176818 A1 | 9/2003 | Schuler et al. | |
| 2003/0208242 A1 | 11/2003 | Harel et al. | |
| 2003/0212439 A1 | 11/2003 | Schuler et al. | |
| 2003/0216791 A1 | 11/2003 | Schuler et al. | |
| 2004/0024428 A1 | 2/2004 | Barrett et al. | |
| 2004/0072731 A1 | 4/2004 | McMichael | |
| 2004/0098062 A1 | 5/2004 | Nachum | |
| 2004/0143296 A1 | 7/2004 | Wang et al. | |
| 2004/0176804 A1 | 9/2004 | Palti | |
| 2004/0230235 A1 | 11/2004 | Schuler et al. | |
| 2004/0230251 A1 | 11/2004 | Schuler et al. | |
| 2004/0236238 A1 | 11/2004 | Schuler et al. | |
| 2004/0260360 A1 | 12/2004 | Schuler et al. | |
| 2005/0010250 A1 | 1/2005 | Schuler et al. | |
| 2005/0021090 A1 | 1/2005 | Schuler et al. | |
| 2005/0033376 A1 | 2/2005 | Whitehurst | |
| 2005/0049655 A1 | 3/2005 | Boveja et al. | |
| 2005/0113879 A1 | 5/2005 | Schuler et al. | |
| 2005/0153885 A1 | 7/2005 | Yun et al. | |
| 2005/0171574 A1 | 8/2005 | Rubinsky et al. | |
| 2005/0192644 A1 | 9/2005 | Boveja et al. | |
| 2005/0197600 A1 | 9/2005 | Schuler et al. | |
| 2005/0222646 A1 | 10/2005 | Kroll et al. | |
| 2005/0239047 A1 | 10/2005 | Gimzewski et al. | |
| 2005/0240253 A1 | 10/2005 | Tyler et al. | |
| 2005/0251061 A1 | 11/2005 | Schuler et al. | |
| 2005/0261601 A1 | 11/2005 | Schuler et al. | |
| 2005/0261747 A1 | 11/2005 | Schuler et al. | |
| 2005/0288732 A1 | 12/2005 | Schuler et al. | |
| 2006/0084942 A1 | 4/2006 | Kim et al. | |
| 2006/0085049 A1 | 4/2006 | Cory et al. | |
| 2006/0121590 A1 | 6/2006 | Speerli | |
| 2006/0155340 A1 | 7/2006 | Schuler et al. | |
| 2006/0184205 A1 | 8/2006 | Schuler et al. | |
| 2006/0206169 A1 | 9/2006 | Schuler | |
| 2006/0224189 A1 | 10/2006 | Schuler et al. | |
| 2006/0287679 A1 | 12/2006 | Stone | |
| 2007/0187840 A1 | 8/2007 | Dell'Acqua-Bellavilis et al. | |
| 2007/0191887 A1 | 8/2007 | Schuler et al. | |
| 2008/0187909 A1 | 8/2008 | Dai et al. | |
| 2008/0234604 A1 | 9/2008 | Burgmans | |
| 2009/0232740 A1 | 9/2009 | Rishpon et al. | |
| 2009/0326593 A1 | 12/2009 | Schuler | |
| 2010/0016651 A1 | 1/2010 | Sivo | |
| 2010/0114216 A1 | 5/2010 | Krause | |
| 2010/0233021 A1 | 9/2010 | Sliwa et al. | |
| 2010/0286689 A1 | 11/2010 | Schuler et al. | |
| 2011/0098783 A1 | 4/2011 | Schuler | |
| 2011/0130754 A1 | 6/2011 | Schuler et al. | |
| 2011/0270248 A1 | 11/2011 | Schuler et al. | |
| 2012/0136412 A1 | 5/2012 | Schuler | |
| 2012/0184800 A1 | 7/2012 | Brighton | |
| 2012/0277814 A1 | 11/2012 | Schuler | |
| 2012/0277837 A1 | 11/2012 | Schuler | |
| 2013/0096840 A1* | 4/2013 | Osorio | A61B 5/374 702/19 |
| 2013/0261711 A1 | 10/2013 | Sivo | |
| 2013/0325082 A1 | 12/2013 | Schuler | |
| 2014/0228910 A1 | 8/2014 | Schuler et al. | |
| 2014/0343627 A1 | 11/2014 | Schuler | |
| 2014/0350637 A1 | 11/2014 | Schuler | |
| 2015/0231243 A1 | 8/2015 | Schuler | |
| 2015/0258318 A1 | 9/2015 | Schuler | |
| 2015/0297895 A1 | 10/2015 | Schuler | |
| 2015/0313537 A1 | 11/2015 | Schuler | |
| 2015/0374991 A1 | 12/2015 | Morris | |
| 2017/0036032 A1 | 2/2017 | Schuler et al. | |

OTHER PUBLICATIONS

Binggeli, R. et al., "Deficits in Elevating Membrane Potential of Rat Fibrosarcoma Cells after Cell Contact," Cancer Research (1985) 45(1):235-241.

Davalos, R. V. et al., "Tissue ablation with irreversible electroporation," Annals of Biomedical Engineering (2005) 33 (2):223-231, Feb.

Griffin, D. T. et al., "The effects of low-level direct current therapy on a preclinical mammary carcinoma: tumour regression and systemic biochemical sequelae," British Journal of Cancer (1994) 69(5):875-878.

Hu, Q. et al., "Simulations of transient membrane behavior in cell subjected to a high-intensity ultrashort electric pulse", Physical Review E (2005) 71,031914, 9 pages.

Marino, A. A. et al., "Association between Cell Membrane Potential and Breast Cancer", Tumor Biology (1994) 15 (2):82-89.

Nuccitelli, R. et al., "Nanosecond pulsed electric fields cause melanomas to self destruct," Biochemical and Biophysical Research Communications (2006) 343:351-360.

(56) References Cited

OTHER PUBLICATIONS

Von Euler, H. et al., "Cell proliferation and apoptosis in rat mammary cancer after electrochemical treatment (EChT)," Bioelectrochemstry (2004) 62(No. A):57-65, April.
Extended European Search Report in European Application No. EP 09763075.0 dated May 24, 2011.
Extended European Search Report in European Application No. EP 09731826.5 dated Dec. 9, 2011.
Birmingham, K. et al., Bioelectronic medicines: a research roadmap, Nature Review, Drug Discovery (2014) Jun. 13:399-400.
Work Begins to Support Self-Healing of Body and Mind, Outreach@Darpa.mil, Oct. 5, 2015, 3 pages, http://www.darpa.mil/news-events/2015-10-05.
Hodsden, S., DARPA Begins Funding "Electroceutical" Research, Med Device Online, News Feature, Oct. 8, 2015, 2 pages, http://www.meddeviceonline.com/doc/darpa-s-begins-funding-eletroceutic.
Tracey, K. J., Shock Medicine, Scientific American (2015) 312(3):28-35.
Famm, K., Bioeletronic Medicines, Using the Peripheral Nervous Systems to Treat Chronic Disease, GSK, Nov. 14, 2014, 13 pages.
GSK partners with Google on bioelectronic medicine, The Pharmaceutical Journal, Aug. 2, 2016, 2 pages.
Wallace, J., Human Health OrganizationTM Announces Launch of New Corporate Website, Human Health Organization, Sep. 18, 2015, 2 pages.
Tracey, K. J., Molecular Mechanisms of Bioelectronic Medicine, 6th Annual Galien Forum, Oct. 27, 2015, New York City, 4 pages.
Microsemi's New RF Module Speeds Time-to-Market for Implantable Medical Device Designers, Aug. 5, 2015, Microsemi Corporation, 6 pages.
Famm, K., A jump-start for electroceuticals, Nature (2013) Apr. 11, 496:159-161.
Steele, C., James Cameron's Brother Wants to Sell you a 'Vape Phone', PC Mag, Nov. 11, 2015, 11 pages.
Goslin, H., Shock therapy, Pharmatimes.com, Feb. 2016, 5 pages.
GlaxosmithKline teams up with Google sister firm in bioelectronics venture, Aug. 1, 2016, 2 pages.
Wolfe, A., The Future of Bioelectronic Medicine, The Wall Street Journal, Jul. 8, 2016, 5 pages.
Vranks, Company Creates the World's First Vaping Mobile Phone, E-Cig News, Jun. 12, 2015 6 pages.
U.S. Appl. No. 15/179,113, Amendment/Reply filed Mar. 8, 2018.
U.S. Appl. No. 15/179,113, Amendment/Reply filed Feb. 3, 2021.
U.S. Appl. No. 15/179,113, Office Action dated Aug. 14, 2017.
U.S. Appl. No. 15/179,113, Office Action dated Mar. 19, 2018.
U.S. Appl. No. 15/179,113, Notice of Allowance dated Jun. 30, 2021.
U.S. Appl. No. 15/179,113, Notices of References Cited, dated Sep. 5, 2019.
U.S. Appl. No. 15/179,113, Information Disclosure Statement filed Aug. 18, 2016.
U.S. Appl. No. 15/179,113, Notices of References Cited, dated Aug. 14, 2017.
U.S. Appl. No. 15/179,113, Final Rejection dated Dec. 8, 2017.
U.S. Appl. No. 15/179,113, Office Action dated Sep. 5, 2018.
U.S. Appl. No. 15/179,113, Amendment dated Nov. 14, 2017.
U.S. Appl. No. 15/179,113, Amendment filed Jul. 19, 2019.

* cited by examiner

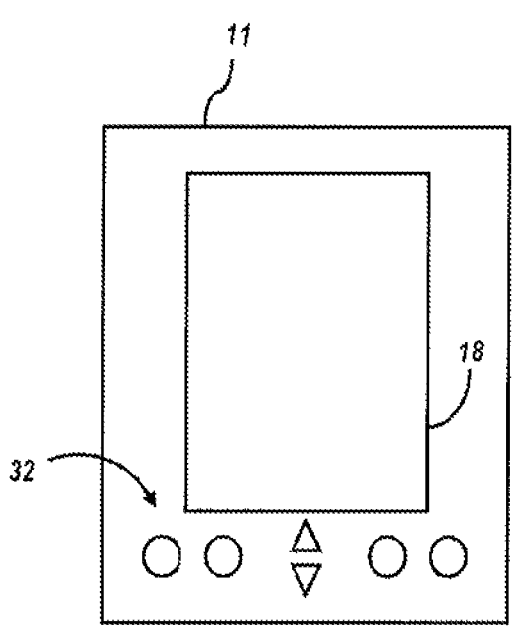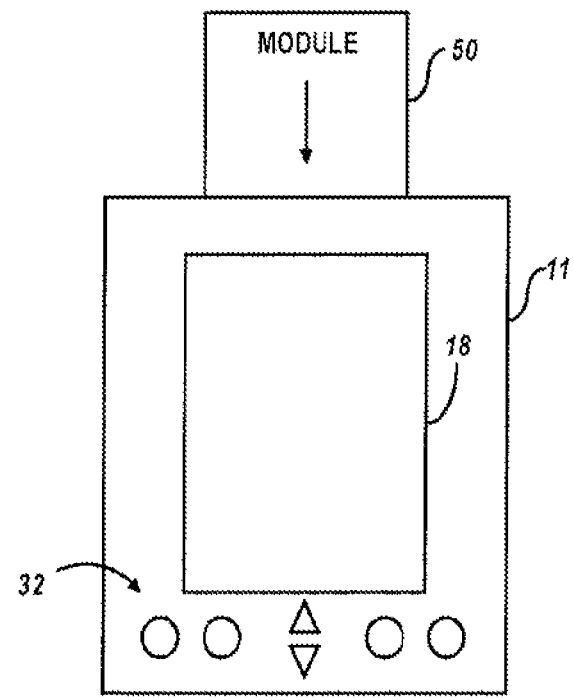
FIG. 2
PRIOR ART
FIG. 3
PRIOR ART

SYSTEMS, METHODS AND APPARATUSES FOR PROVIDING BIOELECTRONIC NEUROCODE-BASED THERAPIES TO MAMMALS

CROSS-REFERENCE TO PATENT APPLICATIONS

This patent application is a continuation of U.S. patent application Ser. No. 15/179,113 entitled "Systems, Methods and Apparatuses for Providing Bioelectronic Neurocode-Based Therapies to Mammals," which was filed on Jun. 10, 2016, and which is incorporated herein by reference in its entirety. U.S. patent application Ser. No. 15/179,113 claims priority under 35 U.S.C. § 119(e) to U.S. Provisional Patent Application Ser. No. 62/202,286, also entitled "Systems, Methods and Apparatuses for Providing Bioelectronic Neurocode-Based Therapies to Mammals," which was filed on Aug. 7, 2015, the disclosure of which is incorporated herein by reference in its entirety.

TECHNICAL FIELD

Embodiments generally relate to the field of bioelectronic medicine or "electroceuticals." Embodiments further relate to systems, methods, and apparatuses for the monitoring and the alteration of conditions in mammals using neurological signal coded ("Neuro-code" or "Neurocode") therapies. Embodiments additionally relate to systems, methods, and apparatuses for inducing apoptosis (programmed cell death) in cancer cells due to reprogramming the intra-cellular operational communication network.

BACKGROUND OF THE INVENTION

Every biological process is also an electrical process. Cells have electrical capabilities and can communicate with each adjacent cell. Normal cells have electro-chemical aspects to manage and operate the intracellular biological mechanisms to control metabolism, reproduction, and cell defense. Not all cells provide a benefit to the human body. Cancer cells, for example, seek to take over normal cells bio-machinery and eventfully destroy them through their communication network. All cell activity is based on communication of low voltage frequency signals, which will be referred to herein as "neurocodes".

The discovery and study of neurological signals (Neurocodes) started in 1780 when Luigi Galvani, an Italian anatomist, attached two dissimilar wires to the spine of a large decapitated frog. Galvani passed a current into the frog by means of a static-electrically-charge rod and made the animal's legs jerk. He determined that nerves conducted electricity and at that moment launched the science of neurophysiology. Galvani's friend, Alessandro Volta, the inventor of the wet-cell battery, commented in 1800 that it was the electrical stimulation from the bi-metal wires which provided the energy to make the frog's legs kick. Thus began the use of stimulating currents to induce neurons to fire their signals, which continues in research universities to this very day.

It never occurred to anyone in those early years that the nerves were actually capable of generating signals on their own without the requirement for some sort of electrical stimulation. It is important to realize that there was no possible way to visualize the cells until after the microscope was invented by Zacharias Jansen in 1590. It wasn't until later in the 1600's that Antony van Leeuwenhoek improved upon that invention and was able to peer at what he called "animalcules." What Leeuwenhock saw were microbes, which was previously unrealized by anyone. He mentioned that there had to be some connection between what he saw and diseases. Early microscopes were not used to study cellular or nervous system structure.

The microscope became more prevalent throughout most university laboratories by 1830 where many biologists began to explore the makeup of life. In Berlin around 1840, Theodor Schwann and Jacob Schleiden established that discrete cells were indeed the architectural building blocks of living tissue, be they plant or animal. This discovery paved the way for others to think about the individual function of many different kinds of cells. Previously, in 1836, Jan Purkinje, a Czech histology and physiologist and his student Gabriel Valentine were able to claim, "The entire nervous system is made up of globules (cells) and continuous primitive fibers (axons)." In 1837, Purkinje was able to describe brain cells with their nuclei and dendrites and the flask-like cells named "Purkinje cells," which are efferent types.

By 1870, very few scientists knew what a neuron really was, much less what it looked like, or how it worked. Therefore, it was still impossible to describe a three-dimensional nervous system at that time in history. But this was to change around 1877 when Camillo Golgi of Italy was able to silver-stain individual neurons so they could be studied under the microscope. Using Golgi's stain, a Spanish professor was able to begin an exhaustive study of the details of neuronal anatomy. Santiago Ramon y Cajal had proposed that neurons were the signaling units for the entire nervous system. This is often referred to as the beginning of the "neuron doctrine." From 1879, Cajal exhaustively studied the brain and many of its structures as he enlarged his understanding of the nervous system. Cajal published numerous technical papers to begin his explanation of the anatomical structure of nerves and the brain. Cajal became recognized throughout Europe by 1889 for his important work. As a result, both Golgi and Cajal shared the Nobel prized in physiology and medicine in 1906.

It was not until the late 20th and early 21st centuries that true bioelectronic medical treatment approaches involving the use of neuro-coded or electrical signaling technologies were possible. More recent advances in technology have allowed for the development of bioelectronic approaches to treating a variety of conditions, including cancer. True bioelectronic medical treatment applications are now possible given advancements in electronics and a better understand of how conditions such as cancer actually function in the human body.

One of the present inventors, Eleanor Schuler, has been heavily involved in the development of the premier bioelectronic technology of our time as outlined in a variety of bioelectronic medical treatment patents and patent applications covering the use of neuro-coded signaling technology. Many patents have already been issued to her for this technology. Schulers intellectual property portfolio implements closed-loop neuromodulation systems that can utilize innate neurophysiological circuits to achieve therapeutic benefits (e.g., "Electrical Prescriptions" as recently referred to by the Defense Advanced Research Projects Agency, DARPA) in a number of medical areas. Examples of only a few of Schuler's patents, which are herein incorporated by reference for their teaching and provide ample background for the science, include: U.S. Pat. No. 8,781,593, entitled "System and Method for Controlling Skeletal Muscles by Means of Neuro-electrical Coded Signals"; U.S. Pat. No.

8,725,246, entitled "Method and System for Modulating Eating Behavior by Means of Neuro-Electrical Coded Signals"; U.S. Pat. No. 8,509,887, entitled "Method to Record, Store and Broadcast Specific Brain Waveforms to Modulate Body Organ Functioning"; U.S. Pat. No. 8,818,502, entitled "Method and System for Regulation of Endocrine and Exocrine Glands by Means of Neuro-Electrical Coded Signals", U.S. Pat. No. 6,957,106, entitled "Implantable Method to Regulate Blood Pressure by Means of Coded Nerve Signals", U.S. Pat. No. 6,751,501, entitled "Method and Apparatus for Myocardial Control", U.S. Pat. No. 6,633,779, entitled "Treatment of Asthma and Respiratory Disease by Means of Electrical Neuro-Receptive Waveforms", and U.S. Pat. No. 6,775,573, entitled "Electrical Method to Control Autonomic Nerve Stimulation of Gastrointestinal Tract".

Further validation of Schuler's bioelectronic technology is evidence by the fact that large pharmaceutical companies and organizations are now moving into the field of bioelectronics, albeit many years after the Schuler's initial patent application filings, and without much in the way of intellectual property. For example, the monolithic international pharmaceutical giant GSK (GlaxoSmithKline) announced in 2013 that It was pursuing an effort toward the development of "electroceutical" or bioelectronic medicine (see "A Jumpstart-Start for Electroceuticals, Nature", 11 Apr. 2013, Vol 496, pp. 159-161, Famm et al). Eleanor Schuler's own research and thinking in the bioelectronic area was captured in patent filings by her many years prior to GSKs 2013 initiative.

To date, the primary approach to treating cancer based on bioelectronic technology has been outlined in further patents and patent application publications by Eleanor Schuler. Such approaches are disclosed in, for example, U.S. Patent Application Publication No. 2010/0286689 entitled "Method and System for Processing Cancer Cell Electrical Signals for Medical Therapy," which published on Nov. 11, 2010; U.S. Patent Application Publication No. 2011/0270248 entitled "System and Method to Elicit Apoptosis in Malignant Tumor Cells for Medical Treatment," which published on Nov. 3, 2011; U.S. Patent Application Publication No. 2011/0130754 entitled "Hybrid Scientific Computer System for Processing Cancer Cell Signals as Medical Therapy," which published on Jun. 2, 2011; and U.S. patent application Ser. No. 12/334,212 entitled "Method to Switch-Off Cancer Cell Electrical Communication Codes as Medical Therapy," which was filed on Dec. 12, 2008. U.S. Patent Application Publication Nos. 2010/0286689; 2011/0270248; and 2011/0180754; and U.S. patent application Ser. No. 12/334,212 are incorporated herein by reference in their entireties. Additionally, Provisional Patent Application Ser. No. 61/940,054 entitled "Encoded Bioelectronic Method and System and Calcium Treatment for Slaying Cancer by Rapid Triggering of Cellular Apoptosis and Karyorrhexis," which was filed on Feb. 14, 2014. All these patents and publications are also incorporated herein by reference in their entirety for their teaching.

What is needed now in light of Schuler's extensive bioelectronic medicine portfolio is improved systems, methods, and apparatuses for providing these electroceutical therapies to mammals. Inventors in the wireless data communications field, Luis Ortiz and Kermit Lopez, have joined with Eleanor Schuler to address the stated need. Messrs. Ortiz and Lopez are the co-inventors of numerous mobile wireless technologies and applications dating back to the year 2000, including U.S. Pat. No. 9,031,537, which is entitled "Electronic Wireless Hand Held Multimedia Device", which is also incorporated herein by reference for its teaching of hardware, systems, and processes associated with mobile data communications. Together, the present inventors provide systems, methods, and apparatuses for providing bioelectronics therapy to mammals (e.g., humans, pets, livestock, etc.), which will be further described in the detailed specification that follows.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification claims, drawings, and abstract as a whole.

It is, therefore, one aspect of the disclosed embodiments to provide for improved systems, methods, and apparatuses for monitoring bioelectronic neurocode-based) signals associated with organ function in mammals and providing bioelectronic therapy to mammals based on monitored conditions.

It is yet another aspect of the disclosed embodiments to provide for improved systems, methods, and apparatuses for treating cancer. The treatment time for causing apoptosis, excitotoxicity, or osmotic-shock to cancer cells and/or malignant tumors can be from as little as less than 20 minutes, and up to many hours, depending on the size and location of the target tumor. The procedure described can also be utilized to treat malignant tumors as well as benign tumors such as uterine fibroid or muscle and limb tumors.

It is another aspect of the present invention that a system can include a wireless computing device that can be in wireless communication with at least one mammal implantable controller ("NC") that includes wireless module supporting communications in close proximity with the wireless computing device. It is also a feature that the wireless computing device can be provided in the form of a mobile device (e.g., in form factor of a smartphone, tablet) serving as a treatment computer.

It is yet another feature of the present invention that the handheld computer has a processor and memory and can record signals monitored by the at least one mammal implantable controller and provided feedback in the form of bioelectronic signals (neurocodes) via the wireless module associated with the at least one mammal implantable controller.

It is yet another feature of the present invention that bioelectronic signals can be provided by either wired or wireless communication to an organ in response to monitoring. Wired communication of bioelectronic signals can be provided via a probe connectable by wire to the mobile device that can enter a mammal's body and contact a targeted organ or region for the administration of bioelectronic therapy. Wireless communication of bioelectronic signals can be provided to an organ via communication with at least one mammal implantable controller that can be further connected (e.g., via internal probe connection) to the organ or region in order to receive the neurocodes wirelessly from the wireless device located a short distance outside the mammal.

In yet another embodiment, bioelectronics signals can be obtained by a mobile device (e.g., a smartphone or tablet supporting secure wireless communications with remote resources via Wi-Fi or cellular communications) from a remote treatment server via a data communications network based on a monitored condition. The monitored condition can be monitored in real-time in accordance with features of the present invention or via traditional monitoring means (e.g., recordation of vitals), and can be communicated to the remote server securely over the data communications network via the mobile device.

It is yet another feature of the present invention that a remote treatment server can provide neurocodes to MICs via either mobile devices or facility installed treatment pods having short range wireless capabilities to communicate with MICs, and the ability to communicate with a remote treatment server or mobile device either wirelessly or via wired data connection.

It is yet another feature of the present invention for more than one treatment pod to be installed in a facility in a manner to provide monitoring and communications with MICs that may be implanted in more than one mammal (e.g., several patients in a treatment facility or hospital).

It is yet another embodiment, mammal implantable controllers ("MICs") can be implantable in a mammal and support radio frequency (RF) communication with a mobile device or other monitoring devices (stationary monitoring pods installed in treatment facilities). A MIC can include a wireless module supporting secure communications in close proximity with the monitoring device (mobile device or pod). It is also a feature that the MIC can be recharged electromagnetically while implanted in a mammal, thereby avoiding openings in the skin of a mammal's body for connection or wiring. A MIC can also include monitoring capabilities via a monitoring module adapted for targeted monitoring of a certain conditions (e.g., insulin, heart rate, blood oxygen), and can provide bioelectronic signals to target organs or regions in the mammal via an associated or integrated neurocode module. Probes can connect a MIC and a target organ or region and also remain implantable within the mammal.

These and other features and embodiments of the present invention will become apparent to the skilled after reading the following detailed description and the appended claims.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the principles of the present invention.

FIG. 2, labeled as prior art, illustrates a pictorial representation a mobile device, and which can be implemented in accordance with an alternative embodiment;

FIG. 3, labeled as prior art, illustrates another pictorial representation of a mobile device including a removable cartridge;

DETAILED DESCRIPTION

Figure 1A:
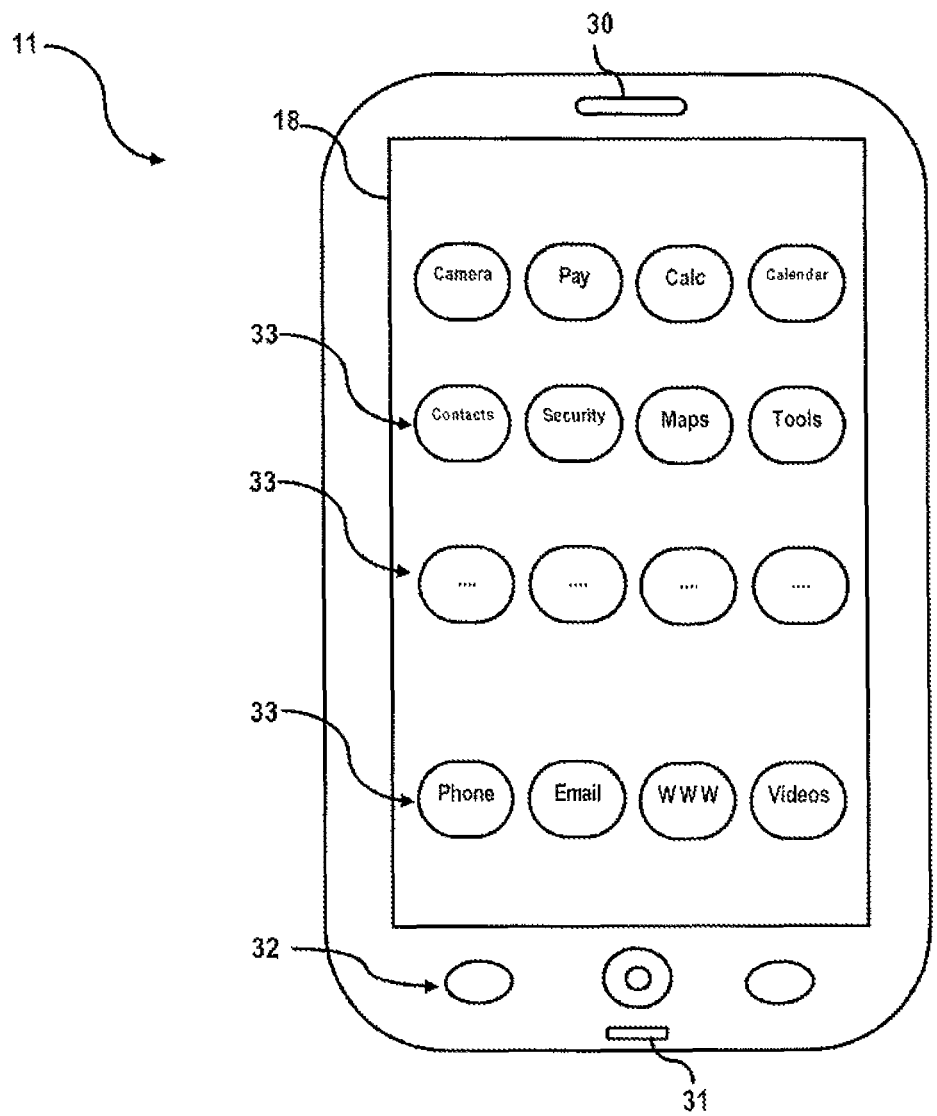
FIGS. 1(*a*), 1(*b*) and 1(*c*), labeled as prior art, illustrates a pictorial drawing of a mobile device.

The particular values and configurations discussed in these non-limiting examples can be varied and are cited merely to illustrate at least one embodiment and are not intended to limit the scope thereof.

The disclosed embodiments generally cover a number of varying embodiments including, for example, systems and methods used for enabling bodily/organ function, or the rapid destruction of malignant tumors by excitotoxicity osmotic-shock medical tactics. Particular treatments are described in the patent documents by Eleanor Schuler, which have been identified in the Background and are incorporated by reference for their teaching. It should be appreciated that the systems and methods described herein can generally apply to monitoring of any bodily functions and the application of any therapies that may be developed and apply to all mammals. For example, it is envisaged that the present invention can be used to apply bioelectronics therapies to cattle for promoting development of a cattle heard, and to race horses to encourage or affect muscular development.

Electronic wireless hand held devices ("mobile devices"), such as data/video-enabled cellular telephones (often referred to as "mobile phones" or "smartphones"), tablet computers, and other portable hand held wireless data-enabled devices have become a part of everyday life. Such mobile device are capable of multimedia data transmission and retrieval from multiple networks and wireless connections including: cellular (including 4G/LTE), 802.11 WiFi networks, short range radio frequency, and/or line of sight communications standards and networks such those that are standardized including Bluetooth, Bluetooth LE, IrDA (infrared), RFID, NFC, and other proprietary secure means that are not yet standardized. Many current mobile devices are capable of determining location information and directions using GPS and by displaying maps retrieved from remote servers (e.g., via the Internet), include touch sensitive display screens, and incorporate high-resolution cameras. Mobile devices are capable of moving data to/from, and operating with, removable cartridges (e.g., external memory, smart card, card-based application modules and electronics) and/or via wireless communication to neighboring devices U.S. Pat. No. 9,031,537, which has been incorporated by reference, is an example of an existing mobile device.

Unlike personal computers, which are general-purpose devices geared towards refining and processing information, modern mobile communication devices are designed to capture, store, and display information originating from various sources while a user is "on the go" or otherwise mobile. Additionally, while a certain level of skill is required to use a personal computer effectively, mobile devices are designed with the novice and non-computer user in mind and are therefore intuitively easy to use. A typical smartphone or tablet includes a microprocessor, memory unit, a display, associated encoder circuitry, and a user interface generally provided in the form of a keyboard and selector buttons. Many mobile devices in the form of smartphones and tablets can optionally contain an infrared emitter and wireless receiver. A graphical user interface permits a user to store, retrieve, and manipulate data via an interactive touch-sensitive display. A mobile device can also include software that enables software applications for using a calendar, directory, calculator, games, and one or more multimedia programs. The calendar typically provides dates organized as rows and columns in the usual form. A directory contains entries consisting of a name field and a free form alphanumeric text field that can contain company names, addresses, telephone and fax numbers, email addresses, etc. Games and multimedia software features can vary.

A menu of icons displayed via the graphical user interface as part of the touch sensitive screen can permit a user to choose particular functions and directories. Some mobile devices come equipped with a stylus, which is a plastic-tipped pen that a user utilizes to write digitally on the display area and tap particular graphically displayed icons; although a user's figure nail can accomplish the same. Each icon is indicative of a particular activity or function. Touch screen interfaces, however, are also increasingly being implemented with mobile devices to permit a user to activate software modules in the form of routines and subroutines operable therein.

Referring to FIG. 1(a), which has been labeled as prior art, a pictorial representation is presented of a mobile device 11, which can be implemented in accordance with a preferred embodiment. The mobile device is shown in a familiar "smartphone" form factor. Data can be transferred to and from the mobile device 11 via wireless data communications. Note that as utilized herein, the term "data" as utilized herein generally refers to signals that can be presented in the form of text, voice, graphics, and/or video, but can include other types of data such as software, security codes, encryption, decryption, etc. Such data can include, for example, "multimedia data" such as video, voice audio, etc.

In general, the mobile device 11 can include a touch sensitive display screen 18, a speaker 30, a microphone 31, and one or more control buttons 32 for controlling some operations of device 11. The device 11 depicted in FIG. 1(a) can be a device, such as, for example, a smartphone capable of communicating with a wireless local area network, and so forth. In this respect, the mobile device 11 can be implemented with touch screen capabilities associated with the display screen 18. Display screen 18 can be configured to display data including video and text and icons 33 operable as soft buttons providing options and action by the mobile device 11 when selected by a user.

Figure 1B:
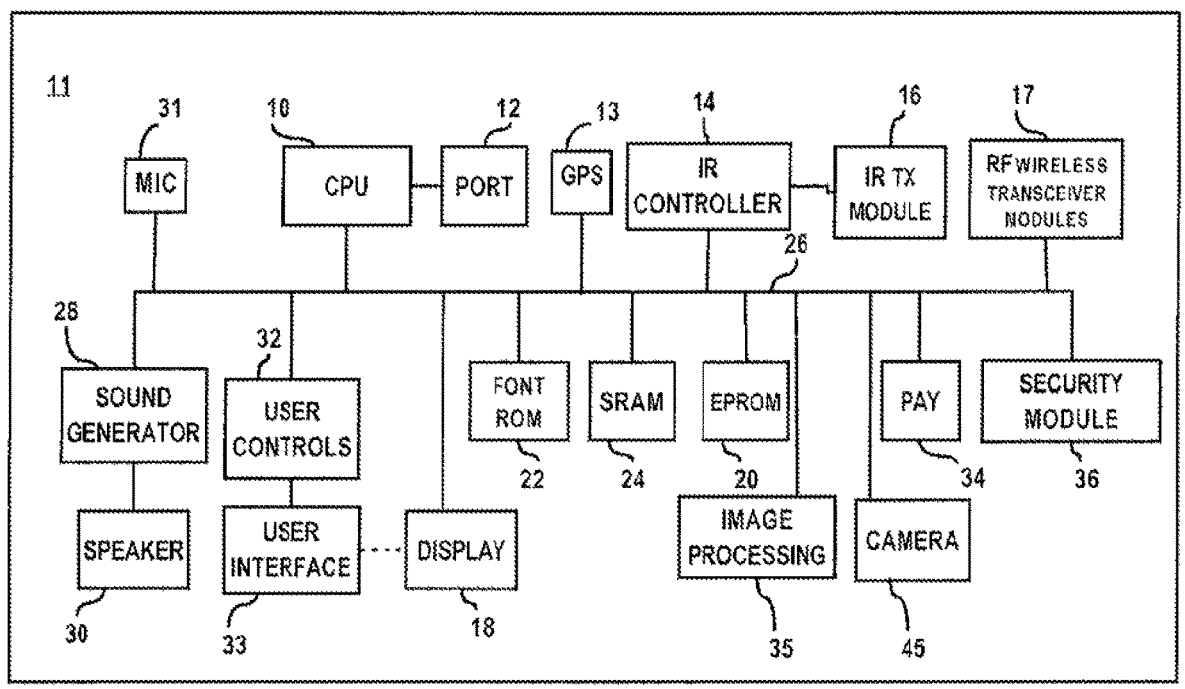

FIG. 1(b), labeled as prior art, depicts a schematic diagram illustrating a general hardware configuration of a mobile device 11 which can be implemented in accordance with an embodiment. The diagram depicted in FIG. 1(b) illustrates a variety of hardware configurations and components/modules, which can be utilized to implement one possible embodiment of the mobile device 11. Those skilled in the art can appreciate, however, that other hardware configurations with less or more hardware and/or modules can be utilized in carrying out the mobile device 11 of the present invention, as will be further described herein.

The mobile device 11 can be capable of carrying out a variety of functionalities. For example, microprocessor shown as CPU 10 of the mobile device 11 can function as a main controller operating under the control of operating clocks supplied from a clock oscillator. CPU 10 can be configured as, for example, a microprocessor. Such a microprocessor can be configured to facilitate operation of and communicate by the electronic wireless hand held multimedia device 11. External pins of CPU 10 can be coupled to an internal bus 26 so that it can be interconnected to respective components.

The mobile device 11 can also be configured to include memories such as, for example, SRAM 24 which can be provided as a writeable memory that does not require a refresh operation and can be generally utilized as a working area of CPU 10, SRAM (Static RAM) is generally a form of semiconductor memory (RAM) based on a logic circuit known as a flip-flop, which retains information as long as there is enough power to run the device. Font ROM 22 can be configured as a read only memory for storing character images (e.g., icons and font) displayable on a display 18, which can be implemented as, for example, a touch sensitive display screen. Example types of displays that can be utilized in accordance with display 18 include, for example, a TFT active matrix display, an illuminated LCD (Liquid Crystal Display), or other small-scaled displays being developed or available in the art in compact form.

CPU 10 can be utilized to drive display 18 utilizing, among other media, font images from Font ROM 22 and images transmitted as data through wireless unit 17 and processed by image-processing unit 35. EPROM 20 can be configured as a read only memory that is generally erasable under certain conditions and can be utilized for permanently storing control codes for operating respective hardware components and security data, such as a serial number. A camera capable of capturing video and pictures can be provided and can also work in conjunction with image processing unit 35.

IR controller 14 when provided can be generally configured as a dedicated controller for processing infrared codes transmitted/received by an IR transceiver module 16 and for capturing the same as computer data. Wireless unit 17 can be generally configured as a dedicated controller and transceiver module for processing all wireless data transmitted from and to a wireless communications network, such as wireless communication network 152, which is described in greater detail herein, but not shown in FIG. 1(b).

Figure 1C:
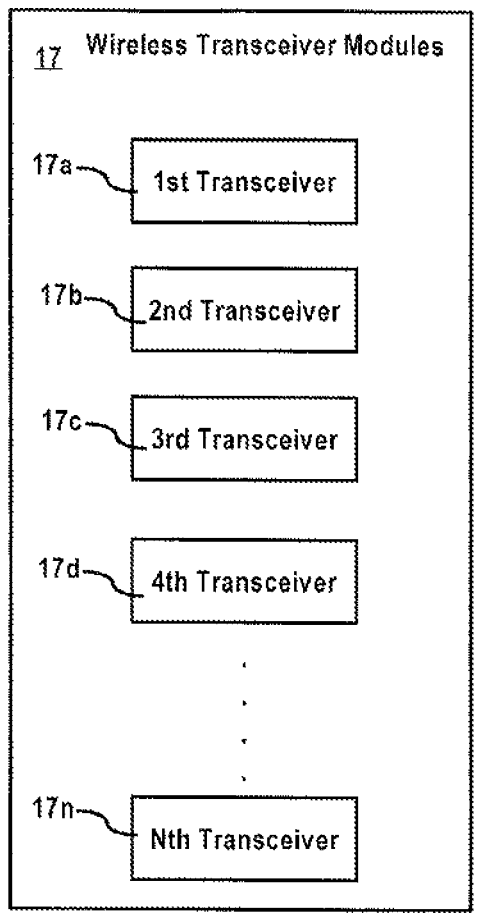

Note that the radio frequency (RF) wireless transceiver modules 17 (i.e., transceiver module) can constitute more than one wireless transceiver (e.g., multiple transceivers) or a wireless module with multiple transceivers capability and formed separately or combined on an ASIC or DSP circuit. For example, FIG. 1(c), labeled as prior art, illustrates a block diagram of RF wireless transceiver modules 17 configured for use with the electronic wireless hand held multimedia device 11, in accordance with an alternative embodiment, including, for example, a first transceiver module 17a, a second transceiver module 17b, a third transceiver module 17c, a fourth transceiver module 17d, and up to an "n.sup.th" transceiver module, and so on.

The first wireless transceiver module 17a can be configured, for example, to support hi-directional data communications of the mobile device 11 with remote data resources (e.g., servers) over cellular data telecommunications networks. Wireless unit/transceiver module 17 can also include the second wireless transceiver module 17b configured to support bi-directional data communications of the mobile device 11 with remote data resources over a wireless local area network (e.g., 80211/Wifi). Additionally, wireless transceiver module 17 can include the third wireless transceiver module 17c configured to support bi-directional data communications of the mobile device 11 over a direct wireless connection with electronic devices located at short range that can be established, for example, within up to five feet, or within x to a hundred foot range from the mobile device 11. Additionally, wireless unit/transceiver module 17 can include the fourth wireless transceiver module 17d configured to support hi-directional data communications of the mobile device 11 over an infrared wireless connection with electronic devices located at line of sight (or "visible") range, which can reasonably be within up to a fifty foot range from the electronic wireless hand held multimedia device 11. It can be appreciated that other variations for wireless transceiver module 17 can also be provided, such as standardized Bluetooth, NFC, Zigbee, etc., and proprietary RF protocols that may be developed for specialized applications.

Referring back to FIG. 1(b), port 12 can be connected to CPU 10 and can be temporarily attached, for example, to a docking station to transmit information to and from the mobile device 11 to other devices, such as personal computers, points of sale such as retail cash registers, electronic kiosk devices, and so forth. In light of the present invention, port 12 can also be connected to external probes and external sensors for monitoring or providing data. Port 12 can also be configured, for example to link with a modem, cradle, or docking station, which is well known in the art, and can permit network devices, a personal computer, or other computing devices to communicate with mobile device 11.

User controls 32 can permit a user to enter data to mobile device 11 and/or initiate particular processing operations via CPU 10. A user interface 33 can be linked to user controls 32 to permit a user to access and manipulate electronic wireless hand held multimedia device 11 for a particular purpose, such as, for example, viewing video images on display 18. Those skilled in the art will appreciate that user interface 33 can be implemented as a touch screen manipulated user interface, as indicated by the dashed lines linking display 18 with user interface 33. User interface 33 can be configured to accept user input into the mobile device 11. In addition, CPU 10 can cause a sound generator 28 to generate sounds of predetermined frequencies from a speaker 30. Speaker 30 can be utilized to produce music and other audio information associated with video data transmitted to mobile device 11 from an outside source.

Additionally, a GPS (Global Positioning System) module 13 can be included in the mobile device and can be connected to bus 26. GPS module 13 can be configured to provide location information for the mobile device 11 and can operate with mapping software and resources to provide navigable directions on the display screen 18 to the user, which can be referred to as GPS mapping.

Those skilled in the art can appreciate that additional electronic circuits or the like other than, or in addition to, those illustrated in FIG. 1 can be required to construct mobile device 11. Mobile devices can be modified to (e.g., with proper authentication, filters, security codes, biometrics or the like) to receive RF transmissions from at least one source (e.g., remote server, a wireless camera, or data from a camera transmitted wirelessly through a local data transmitter using Wi-Fi). Those skilled in the art can thus appreciate that because of the brevity of the drawings described herein, only a portion of the connections between the illustrated hardware blocks is generally depicted. In addition, those skilled in the art will appreciate that electronic wireless hand held multimedia device 11 can be implemented as a specific type of a hand held mobile device, such as a Smartphone, Personal Digital Assistant (PDA), paging device, LTE-enabled mobile phone, and other associated hand held computing devices well known in the art.

Mobile device 11 can be configured to permit images, such as broadcasted video images or other multimedia data, to be displayed on display 18 for a user to view. Electronic wireless hand held multimedia device 11 thus includes an image-processing unit 35 for processing images transmitted as data to electronic wireless hand held multimedia device 11 through wireless unit 17. A payment module 34 can be implemented in the device 11 to enable the management of payment transactions which can be negotiated wirelessly through the device, for example, by enabling hand held device users to be billed a transaction fee via bank accounts (e.g., ATM, Debit and Credit cards) billing via communication service accounts or arrangements, prepaid services, and other authorized account-related billing arrangements. Payment can be made directly to a wireless point of sale and/or over data networks. A security module can be provided to enable protected data retrieval and management by enabling the use of passcodes, passwords, and/or biometrics and communications security during hand held device communications. A video camera and video transmission capabilities enable a user to capture, store, process, and transmit video and take pictures. Payment module 34 can be linked through internal bus 26 to CPU 10. Additionally, a security module 36 can be utilized to process proper security codes to thereby ensure data (e.g., multimedia data) transferred to and from electronic wireless hand held multimedia device 11 can be secured and/or access can be permitted. Security unit 36 can be implemented as an optional feature of electronic wireless hand held multimedia device 11. Security unit 36 can also be configured with routines or subroutines that are processed by CPU 10, and which prevent wireless data from being transmitted/received from electronic wireless hand held multimedia device 11 beyond a particular frequency range, outside of a particular geographical area associated with a local wireless network, or absent authorized authorization codes (e.g., decryption).

Those skilled in the art can appreciate that although a mobile device 11 is generally illustrated in FIG. 1(a), other mobile devices can be implemented as a wireless application protocol (WAP), web-enabled cellular hand held device, such as a PDA, wireless telephone, or a combination thereof. Mobile device 11 can be configured with features of combination cellular telephone/PDA devices. Mobile device can also permit users to access e-mail, store calendars, and contact databases. Mobile device 11 can also be configured to include the use of multi-RF (Radio Frequency) receiver-enabled hand held television viewing device. Regardless of the type of hand held device implemented, it can be expected that such a hand held devices will be adapted to receive and process data via image-processing unit 35 for ultimate display as moving images (video) on display 18, in accordance with the present invention. Image-processing unit 35 can include image-processing routines, subroutines, software modules, and so forth, which perform image-processing operations.

FIG. 2, labeled as prior art, illustrates a pictorial representation of a mobile device 11, which can be utilized to implement a preferred embodiment. Mobile device 11 includes a display screen 18. Multimedia data (e.g., video, audio, graphics, etc.) broadcast via radio frequency or provided digitally and wirelessly can be displayed on display screen 18 for a user to view. User controls 32 can permit a user to manipulate images or text displayed on display screen 18, such as the buttons on a keyboard provided on most Blackberry devices. A touch screen user interface can be further configured on the display screen 18 with mobile device 11 to permit a user to manipulate images/text displayed on display screen 18.

FIG. 3, labeled as prior art, depicts a pictorial representation of mobile device 11 adapted for receiving a cartridge 50, in accordance with an alternative embodiment. Mobile device 11 of FIG. 3 is generally analogous to mobile device 11 of FIG. 2, the difference being that mobile device 11 of FIG. 3 can be adapted to receive a cartridge bearing software and/or hardware modules (including memory) that permits mobile device 11 of FIG. 3 to function according to specific hardware and/or instructions contained in a memory location within cartridge 50. The alternative embodiment depicted in FIG. 3 thus represents a variation to the embodiment illustrated in FIG. 2.

Cartridge 50 can be configured as a smart card of another appropriate module. Such a smart card can provide, for example, access codes (e.g., decryption) to enable mobile device 11 to receive data broadcasts. Note that as utilized herein, the term "module" can refer to a physical module, such as a cartridge. The term "module" can also refer to electronics and hardware stored on a cartridge. The term "module" can also refer to a software module composed of routines or subroutines that perform a particular function (e.g., an "App"). Those skilled in the art can appreciate the meaning of the term module is based on the context in which the term is utilized. Thus, cartridge 50 can be generally configured as a physical cartridge or smart card. The term "module" as utilized herein can also refer to a software module, depending on the context of the discussion thereof.

To illustrate the use of a physical module, such as module 50, assume that a user can possess several such physical modules or cartridges. A cartridge, when inserted into mobile device illustrated in FIG. 3, can instruct mobile device 11 to function as a standard smartphone, such as an iPhone or Samsung branded device. Other functions including communications, software, memory, and supplemental circuitry can be provided using a cartridge that can be inserted within and removed from the mobile device 11.

Those skilled in the art can thus appreciate that electronic wireless hand held multimedia device 11 can be adapted to receive and cooperate with cartridge 50. Additionally, mobile device 11 includes display screen 18, which can be similar to display unit 18 of FIG. 1. Electronic wireless hand held multimedia device 11 depicted in FIG. 3 can also include user controls 32. Thus, mobile device 11 can also implement touch screen capabilities through a touch screen user interface integrated with display screen 18.

Assuming cartridge 50 is implemented as a smart card, it is anticipated that similar features can be implemented in accordance with the smart card to insure that hand held device 11 includes touch screen user interface 18 and video viewing capabilities. Smart cards are generally known in the art as credit-card sized plastic cards with an embedded computer chip. The chip can either be a microprocessor with internal memory or a memory chip with non-programmable logic. The chip connection can be configured via direct physical contact or remotely through a contactless electromagnetic interface.

Smart cards can be generally configured as either a contact or contactless smart card, or a combination thereof. A contact smart card requires insertion into a smart card reader (e.g., contained within hand held device 56) with a direct connection to, for example, a conductive micromodule on the surface of the card. Such a micromodule can be generally gold plated. Transmission of commands, data, and card status takes place through such physical contact points.

A contactless card requires only close proximity to a reader. Both the reader and the card can be implemented with antenna means providing a contactless link that permits the devices to communicate with one another. Contactless cards can also maintain internal chip power or an electromagnetic signal (e.g., RF tagging technology). Two additional categories of smart codes, well known in the art, which are based on contact and contactless cards, are the so-called Combi cards and Hybrid cards.

A Hybrid card generally can be equipped with two chips, each with a respective contact and contactless interface. The two chips are not connected, but for many applications, this Hybrid serves the needs of consumers and card issuers. The Combi card can be generally based on a single chip and can be generally configured with both a contact and contactless interface.

Chips utilized in such smart cards are generally based on microprocessor chips or memory chips. Smart cards based on memory chips depend on the security of the card reader for their processing and can be utilized with low to medium security requirements. A microprocessor chip can add, delete, and otherwise manipulate information in its memory. Microprocessor-based memory cards typically contain microprocessor chips with a variety of architectures.

The mobile device 11 of FIGS. 1-3 can be configured as a hand held wireless device adapted for use with a cartridge/module, such as module 50. The cartridge/module 50 can contain the electronics (e.g., tuner, filter, etc.) to allow a hand held device to be adapted for receiving multimedia data. Mobile device 11 includes a display screen 18 for the display of multimedia data. Additionally, display screen 18 of electronic wireless hand held multimedia device 11 can be configured with a touch screen user interface displayable and operable on display screen 18. Display screen 18 can include one or more touch screen areas.

Figure 4:
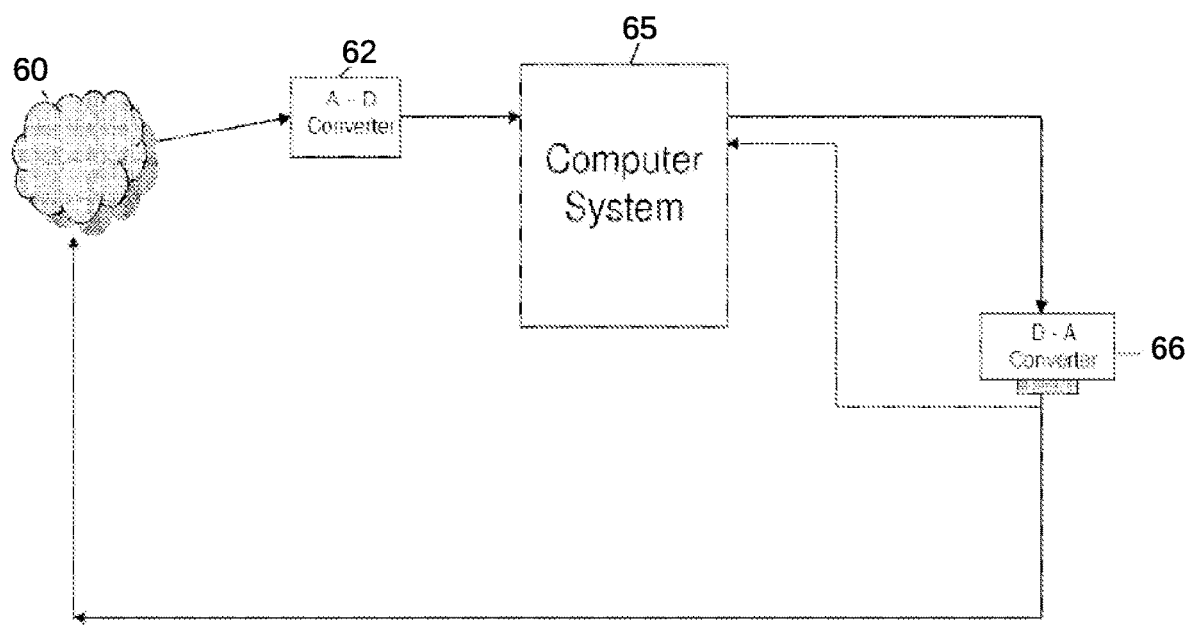
FIG. 4, labeled as prior art, illustrates a block diagram of a desktop computer including neurocode functionality.
Figure 5:
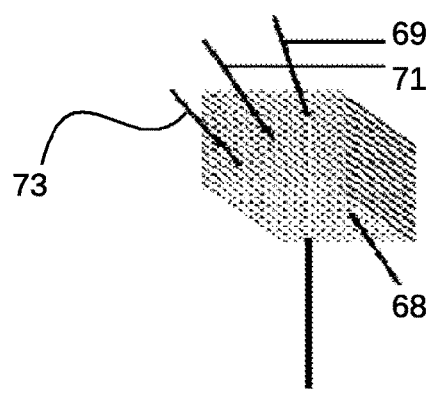
FIG. 5, labeled as prior a illustrates an imulus for delivering treatment to cells.

The following writing with respect to FIGS. 4-5 describes cancer treatment using neurocodes and is being provided only as an example bioelectronic treatment. This example is not meant to be limiting in nature and should not be interpreted as so. The present invention is applicable to all forms of neurocode/bioelectronics treatment.

A cell is the smallest unit of life. Groups of cells make up multi-cellular organisms. The human body is made up of some 100 trillion cells. Cells utilize electrical and chemical signaling in operating interior and exterior mechanisms depending on the composition of the cell. Some cells are operational and signal to the brain and receive signals from the brain to regulate muscles, gland, and vital organs. Other cells only take instructions from the brain while organs and glands confine their cells to dedicated processes concerning the maintenance of life. Certain nerves and their cells are dedicated to sensing internal body status or seek information from outside the body, all with electrically encoded signals. The electrical cellular signal pattern of a malignant as well as a non-malignant cell must be able to be detected, recorded, and it must be reprogrammable to access operational control of critical nucleous activity.

Cancer cells operating as an organized tumor structure do not conduct or exchange signaling processes with normal cells. They do, however, communicate with other cells within a given tumor. They focus on their own interior signaling and metabolism while communicating with adjacent cancer cells. Cancer cells do not participate in any operational functions within a human or animal body except among themselves. Cancer cells do not aid or do anything beneficial for a human body. They are selfish and only live to reproduce and steal nutriment and oxygen from the body in which they reside.

Cancer cells, as they form a malignant tumor, require more blood flow. To accomplish this, they have evolved a way to signal to nearby arterial blood supplies so as to order-up the formation of buds on the artery that ultimately extend into blood vessels that travel over to and pipeline into the tumor. With additional blood flow, the tumor continues to reproduce and extend its dominance over its primary site.

Referring to FIG. 4, labeled as prior art, a cancer cell cluster or tumor is illustrated 60. By means of an imulus or other probe as described by way of example in FIG. 5, the resident electrical signal or signals of the cancer are then provided to a computer system 65 for storing and processing. Typically, the computer system 65 is digital, and in order to accept the electrical signals from the tumor 60, an analog to digital converter 62 is used. If the computer system 65 employed includes an embedded analog to digital converter, the converter 62 can be omitted. It is the computer system 65 in which all of the processing, analysis and generation of confounding electrical signals occurs. In order to treat the tumor 60, the confounding electrical signals are applied directly to the tumor 60 via an imulus or probe after conversion to analog state by a digital to analog converter 66.

The technical approach is to initially develop a number of cancer cell resident electrical signals for different species of cancer and perfect reprogrammed confounding type signals. The user then sorts and reprograms the natural signals of the cancer cell and tinkers with the electrical signatures and coding to finally select appropriate treatment electrical signals, also known as confounding electrical signals. This is followed by devising a library/data-base of treatment signals. The collection of treatment signals may be cataloged as to the species of cancer and anatomical location. During treatment of a cancer, the first step is to identify the species of cancer and then select the proper confounding signal with which treatment will begin. Once the treatment team knows the species such as carcinoma or sarcoma, they select from the computerized library/data-base the most appropriate treatment signal. There are approximately about a total of 200 cancer species in existence. Ultimately, the treatment library will be composed of at least as many definitive cancer confounding, interclusio, or mortifier signals. Carcinoma species is the most common cancer and likely represents something like 50% of all cancerous tumors throughout the body.

Once the cancer cell locations in a patient have been identified, the cancer cellular electrical activity has been recorded and analyzed, and an appropriate response has been determined, the medical staff can develop and initiate a treatment protocol. The protocol will follow established medical procedures with the main objective of applying the proper signals and appropriate electrical energy to the cancerous cells to cause apoptosis. The computer system 60 can contain a low voltage and amperage power supply to ensure the correct voltage and amperage is delivered to the cancerous cells. The electrical energy delivered is less than 1 volt and less than 10 millionths of an amp for a pulsed application on the cancer over a few seconds. The treatment may be repeated. The range of electrical treatment may span upwards of 2 volts and 70 micro amps and as low as one-tenth of a volt or possibly even lower at 2 microamps or even lower into the picoamp range. The treatment time may extend up to 4 minutes or more and is repeatable over days if required. The treatment signals in the form of an electrical signal will have a definable shape and be encoded to confound the natural electrical activity found in the cancer cell plasma membrane wall and within the very interior of the cell proper. With the use of the proper code to shut off cellular electricity, the result is apoptosis of the cancer. Cancer death can begin in less than an hour once its metabolic processes are shut-down. Cell death actually may occur in less than 10 minutes as a human brain cells do when blood circulation or electrical signals are turned off. Natural resuscitation of the cancer cell may be possible if the confounding electrical signal treatment is too brief or incomplete. Otherwise irreversible biological decay will set in as long as the cellular process has been severely damaged by the treatment signals. The body immune system is expected to consume the dead or dying cancer as soon as the outer cell membrane negative electric charge is off or markedly diminished. It is the strong negative outer electrical charge of the cancer cell membrane glycocalyx that keeps the immune cells from attacking since they too are negatively charged and would be repelled from one another. Normal cells have outer coat charges that are usually positive and are therefore accessible to the negatively charged immune system cells.

Treatment can be done with a small cable of total diameter no more than a wooden matchstick. Referring to FIG. 5, labeled as prior art, an imulus or treatment contact unit 68 can be utilized to provide treatment within a mammal body. The imulus can be provided in a small form factor and can contain hundreds or thousands of carbon nanotubes 69, 71, 73, and so forth. The nanotubes 69, 71, 73, etc., may be hollow or partitioned. In addition they may be coated with a metal deposition or chemical that interferes with the glycocalyx strong negative electrical charge. The carbon nanotubes equipped imulus 68 can appear under a microscope like a hair brush. Each nano fiber tube is about one-ten-thousandths of a human hair in diameter. The imulus 68 can be used to both record and apply the treatment signal and may be of different sizes to fit the various cancer clusters. The physical approach to the cancer can be guided by fluoroscopy or other visualization apparatus or system to insure that the treatment is applied properly and completely and is directed at the correct target.

The imulus 68 can be positioned to make contact with the tumor as the primary junction between the computer system 65 and the malignant cellular tumor 60, which is to be treated. Modified nano carbon tubes can also act like an antenna and only need to be in close proximity of the malignancy to send in the interclusio or impulses mortifier codes, Insertable links, implantable antennas, and contact pads or implacable treatment needles of carbon or metal can be in the arsenal of imulus attachments, among others.

It has been preferred that analog computers are used because they are as sensitive and able to record the cancer electrical signals as required. As analog computer developments advance they may be more suitable and be the system of choice in destroying cancer cell life. Otherwise the system as illustrated, if digital, can utilize A-D and D-A converters 62, 66, interfaced with a digital processor in the computer system 65 using appropriate software to control signals for monitoring and delivering treatment.

Examples of other processes that cells naturally perform via bioelectronics signals and which are relevant to neurocode treatment are:
  a. Cell reproduction
  b. Encoding of proteins
  c. Regulation of growth d. Differentiation of the cell
e. Internal cell communication
f. External signaling to other cells
g. Excretion of chemicals
h. On or off control of secretions or excretions
i. Timing of operations for cellular organelles
j. Various levels of signaling within the nucleus
k. Signals between plasma membrane and nucleus
l. Operation of transport mechanisms in cell wall Cell signaling is accomplished by a combination of electrical and chemical interactions. Different types of cells require a varied level of signaling qualities. The creation or generation of a given cells signals begins in the plasma membrane where raw material and chemical ions are taken in from the extracellular matrix to both generate electricity and establish the signal format. The plasma membrane is a sort-of cell wall and the area that takes in the required raw material via its ion channels. Ion channels open and close to allow passage into and from the cell interior. Electrical signals are likely generated in the plasma membrane before they are sent via the cytoskeleton, all about the cell to go and participate and contribute to cell operations.

Figure 6:
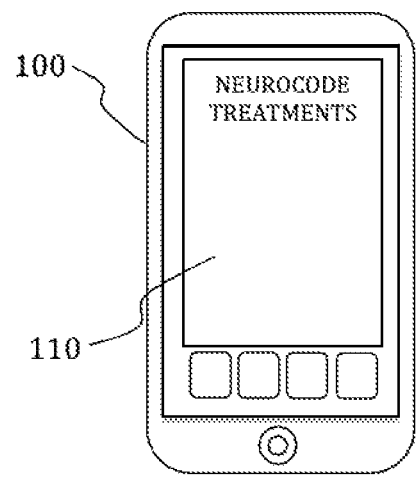
FIG. 6 illustrates a block diagram of a mobile device similar to that illustrated and described with respect to FIGS. 1-3, but including a neurocode module therein.

Referring to FIG. 6, illustrated is a block diagram of a mobile device 100 similar to the mobile device 11 illustrated and described with respect to FIGS. 1-3, but the mobile device 100 of FIG. 6 includes a neurocode module 110 therein. The mobile device 100 can also represent a tablet computer having a neurocode treatment module 110 therein.

Figure 7:
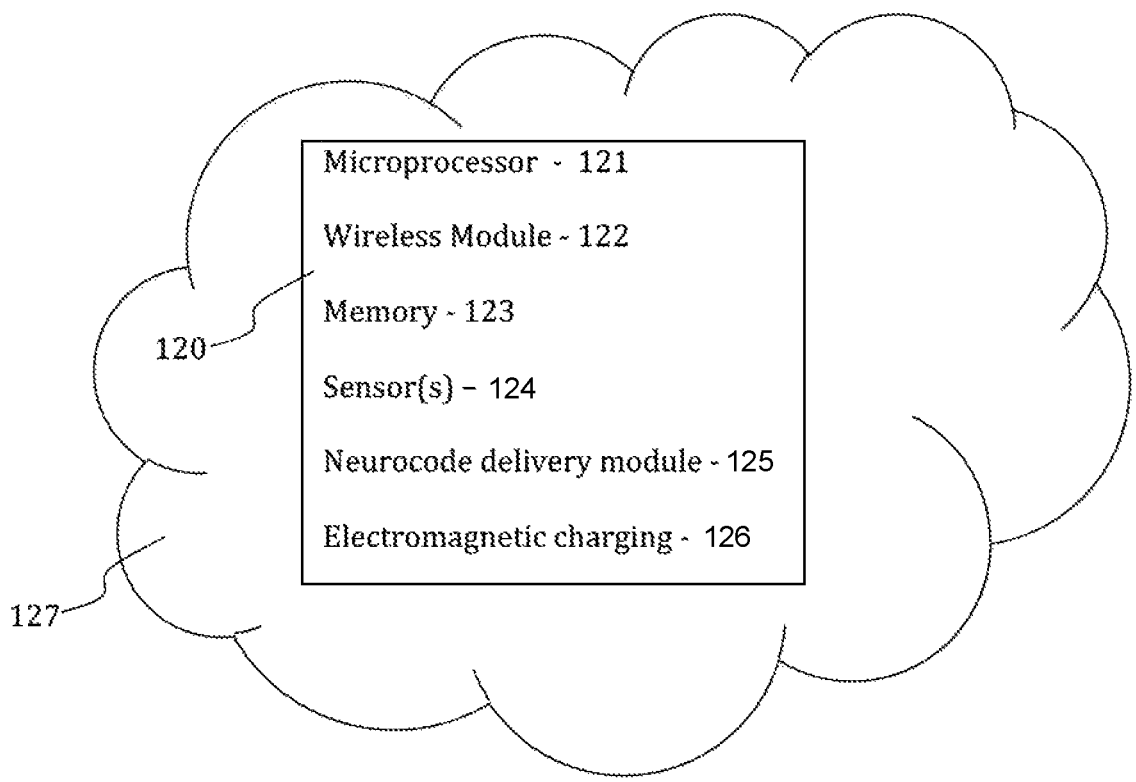
FIG. 7 illustrates a block diagram of a mammal implantable controller (MIC)

Referring to FIG. 7, illustrated is a block diagram of a mammal implantable controller (MIC) 120, which is illustrated by example as being implanted in a mammal body 127. The MIC 120 can include a microprocessor 121 for processing data and running application associated with neurocode treatment, wireless module 122 supporting short range wireless communications with treatment devices (e.g., mobile device 100) located outside the mammal body 127, memory 123 for storing data and onboard applications (e.g., monitoring and therapy administration functions), sensors 124 tied to monitoring body/biological functions, a neurocode delivery module 125 (code specific to monitoring conditions, secure communication, and delivering treatment), and electromagnetic charging hardware 126 (including power supply) enabling the MIC 120 to remain functional and charged with power without invading the mammal body 127 with wires or other apparatuses physically entering the mammal body 127. The MIC 120 can be mostly semiconductor-based and support short-range communications through the mammal body 127 with mobile devices 100 as well as other devices (e.g., facility communication pods described in FIG. 10) to providing data representing conditions of the mammal body collected by sensors/probes also located within the mammal body 127. The MIC can also receive and administer treatment codes (neurocodes) received from outside the mammal body (e.g., via mobile devices or facility communication pods).

Figure 8:
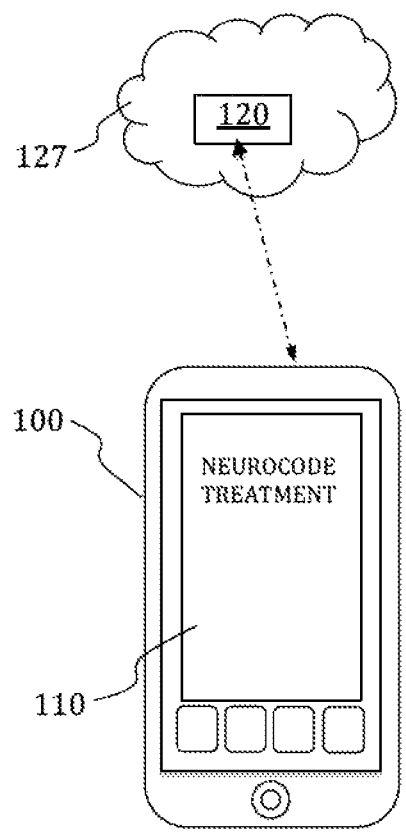
FIG. 8 illustrates a functional diagram of a mobile device such as that in FIG. 6 in short-range wireless communication with at least one mammal implanted controller such as presented in FIG. 7.

Referring to FIG. 8, illustrated is a functional diagram of a mobile device 100 such as that in FIG. 6 in short-range wireless communication with at least one mammal implanted controller (MIC) 120 embedded in a mammal body 127, such as presented in FIG. 7. FIG. 8 illustrates a basic configuration for wirelessly administering neurocode treatment to mammals via MICs 120.

Figure 9:
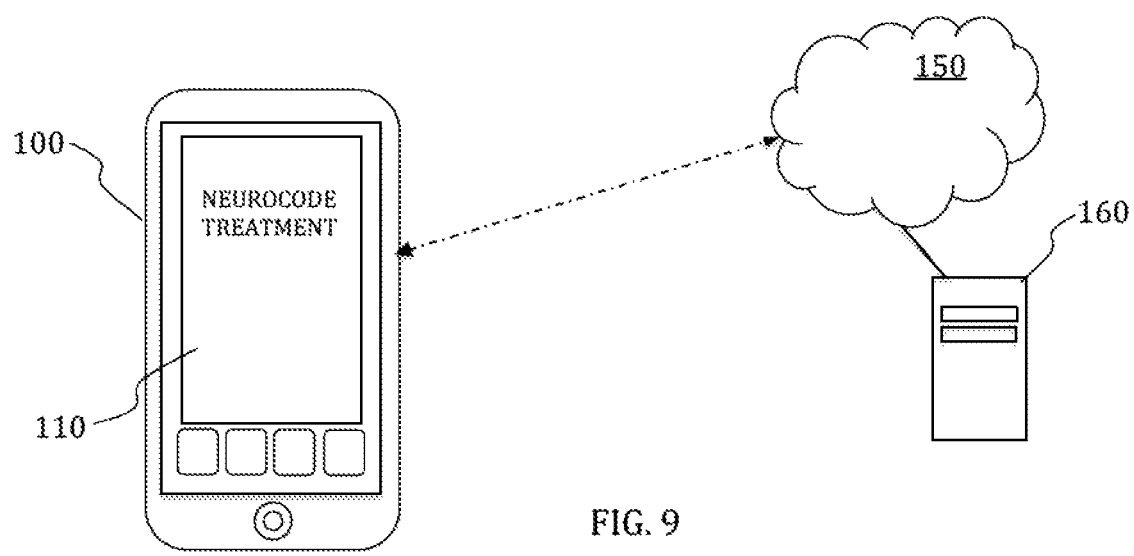
FIG. 9 illustrates a functional diagram of a mobile device in communication with a remote neurocode treatment server via a data communication network.

Referring to FIG. 9, illustrated is a functional diagram of a mobile device 100 in communication with a remote neurocode treatment server 160 via a data communication network 150. Mammal conditions (monitored or obtained externally) can be provided to the remote treatment server 160 for analysis, and treatment neurocodes can be obtained/provided by the treatment server 160 to the mobile device 100 for communication to at least one MIC (as in FIG. 8) for treatment of a mammal.

Figure 10:
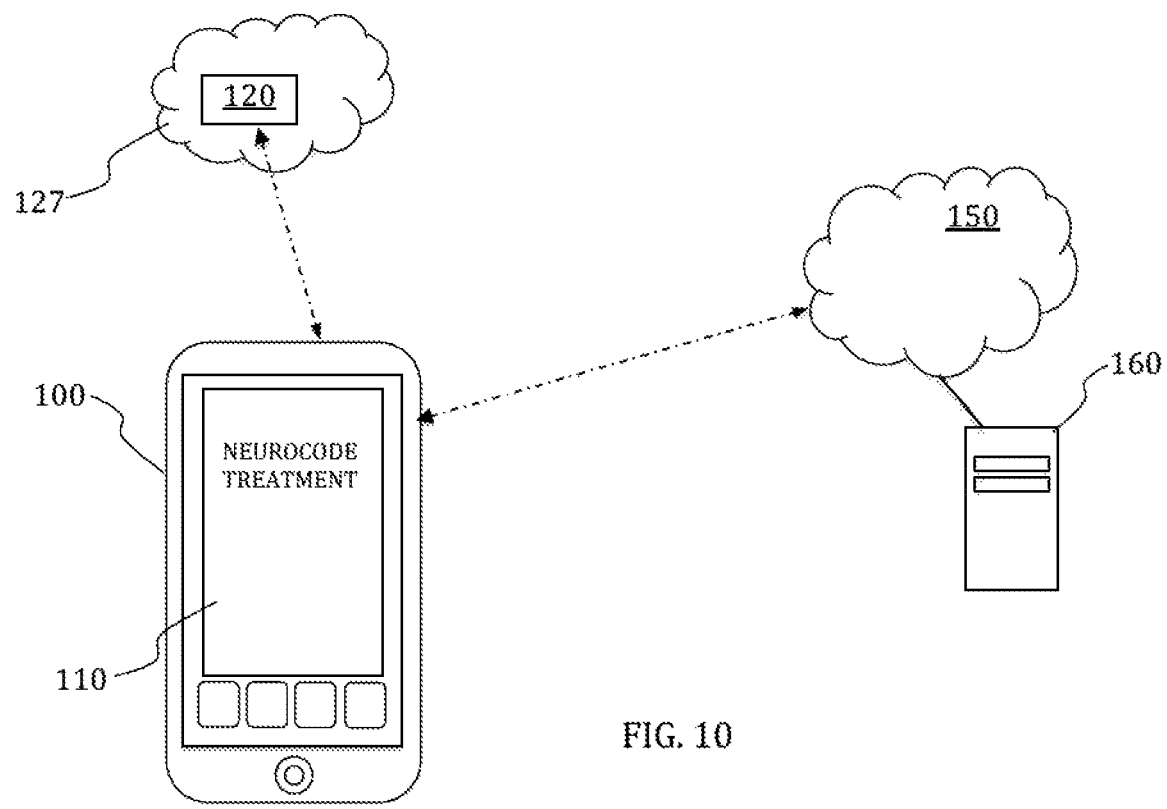
FIG. 10 illustrates a functional diagram of the mobile device of FIG. 6 in communication with a remote server (e.g., neurocode treatment server) via a data communication network, and also in communication with a mammal implanted controller.

Referring to FIG. 10, illustrated is a functional diagram of the mobile device 100 containing a neurocode treatment module 110 (as described in FIG. 6) in communication with a remote neurocode treatment server 160 via a data communication network 150, and also in communication with a mammal implanted controller 120. Monitored data obtained from the MIC 120 by the mobile device 100, and/or provided to the mobile device by treatment personnel, can be communicated wirelessly over data network 150 to the remote treatment server 160. The data can be analyzed by the remote treatment server 160, and neurocodes can be feedback to the mobile device from the treatment server 160, based on the analysis, for wireless transmission to the MIC 120, which can then administer the neurocodes as treatment to the mammal body (e.g., to an organ or treatment area).

Figure 11:
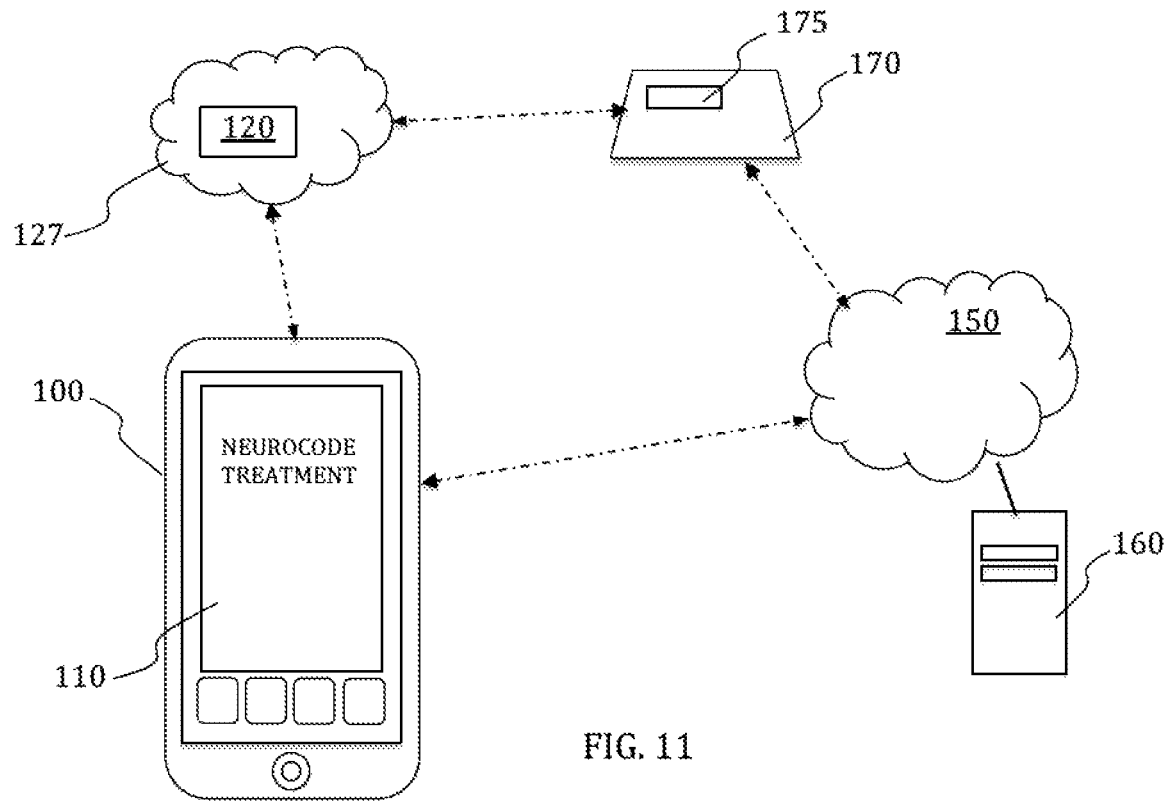
FIGS. 11-14 illustrate flow diagrams for methods of monitoring and providing neurocode based bioelectronic therapy to mammal in accordance with the teachings of the present contained herein.

Referring to FIG. 11, illustrated is a functional diagram of a mobile device in communication with a MIC 120 and a remote treatment server 160. Also shown in FIG. 11 is a resident treatment pod 170 including a neurocode treatment module integrated 175 therein. At least one resident treatment pod 170 can be installed in a facility, such as a treatment facility or hospital, where a patient or patients undergoing neurocode therapy is/are located. The resident treatment pod 170 can communicate with the remote treatment server 160 via a data network 150 similarly to how the mobile device 100 can. The resident treatment pod 170 can also communicate wirelessly with MIC 120, which can be associated with patients/guests to the facility. Monitored mammal conditions from the MIC 120 and treatment neurocodes provided to the MIC 120 for administration to the mammal can be facilitated exclusively through the resident treatment pod 170, or as a backup or supplement to the mobile device 100. It can be appreciated that, in a facility such as a hospital, a treating physician can obtain monitored conditions from a patient's MIC 120 using a mobile device 100 (e.g., tablet computer used by doctor on rounds in a hospital) and can provide the conditions as data to a remote treating server 160 over the data network 150. The server can then analyze and provide treatment codes as feedback directly to the patient via the resident treatment pod 170, or can provide analysis to the physician via his mobile device 100 for further evaluation by the physician. A physician may determine that treatment codes are necessary based on analysis of the treatment server data and can provide treatment codes directly to the MIC, or can order treatment codes at the treatment server for administration (either once or on a treatment schedule) for delivery to the MIC via a resident treatment pod 170.

It should also be appreciated that resident treatment pods can be distributed throughout a facility for tracking, monitoring, and treatment of patients (e.g., such as residents roaming about in a nursing home or patients being moved within a hospital). By doing this, patients are assured to continue monitoring and obtain neurocode-based treatments. Furthermore, the physician and facility can maintain a treatment log for the patient record, insurance purposes, and for billing purposes.

Figure 12:
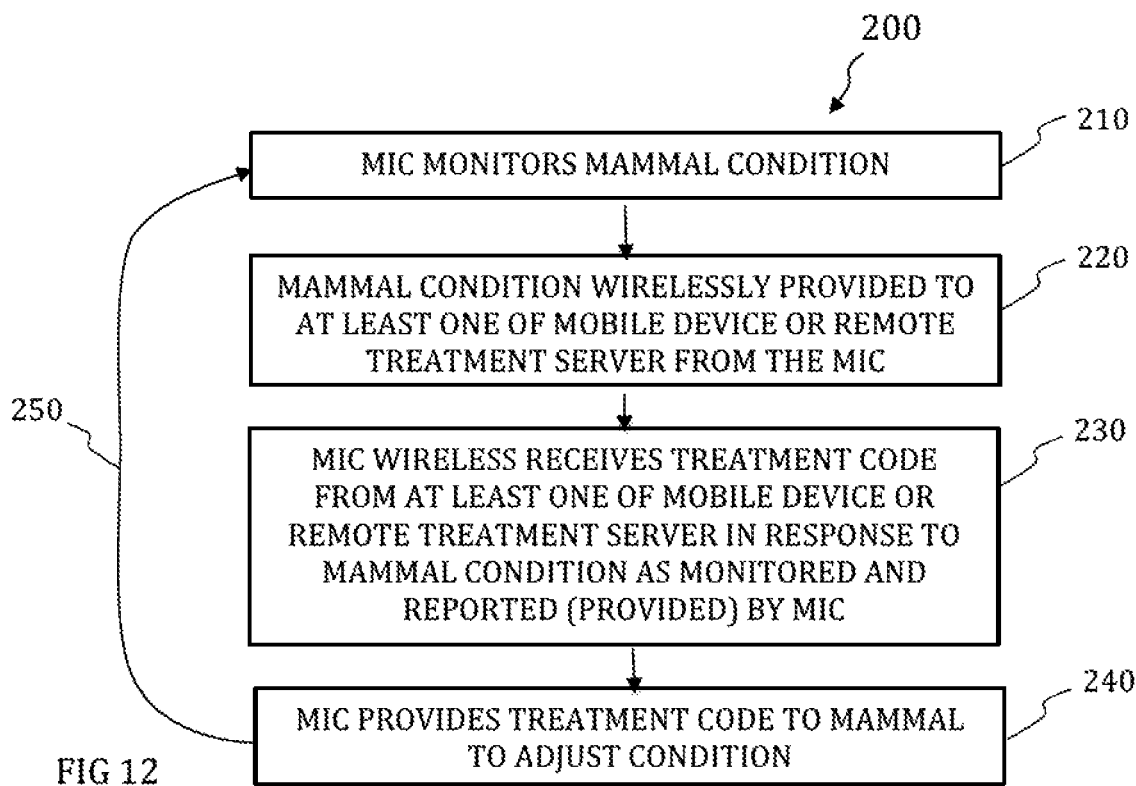
Figure 13:
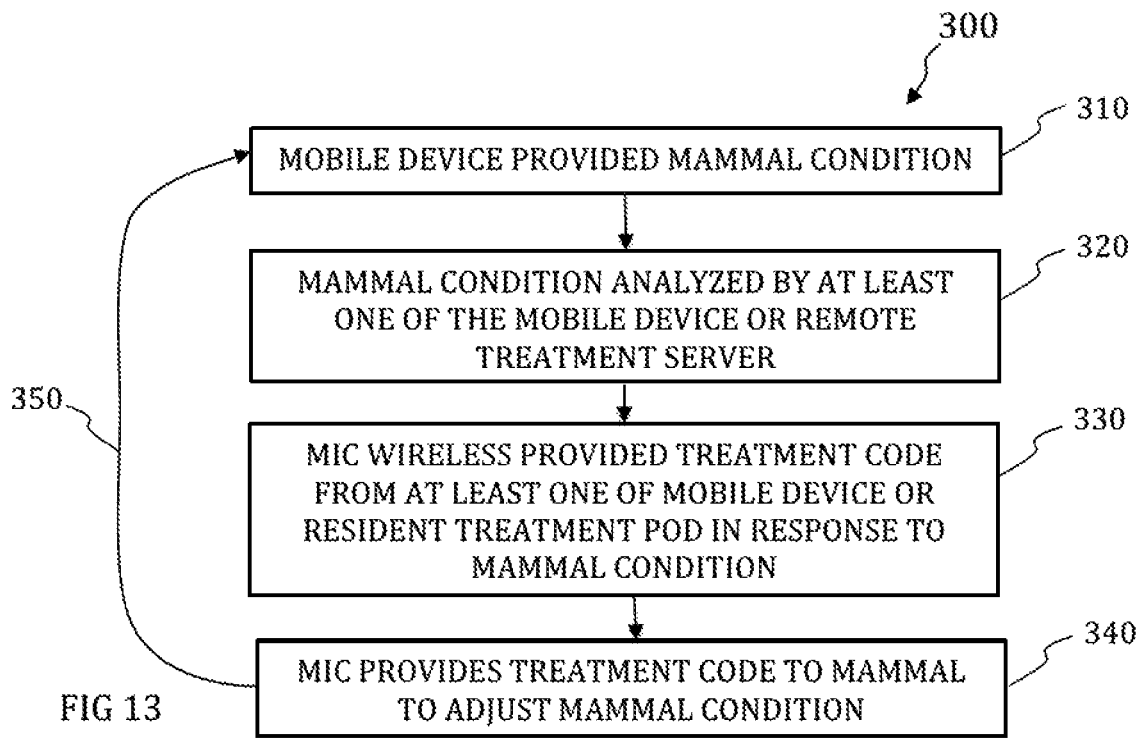
Figure 14:
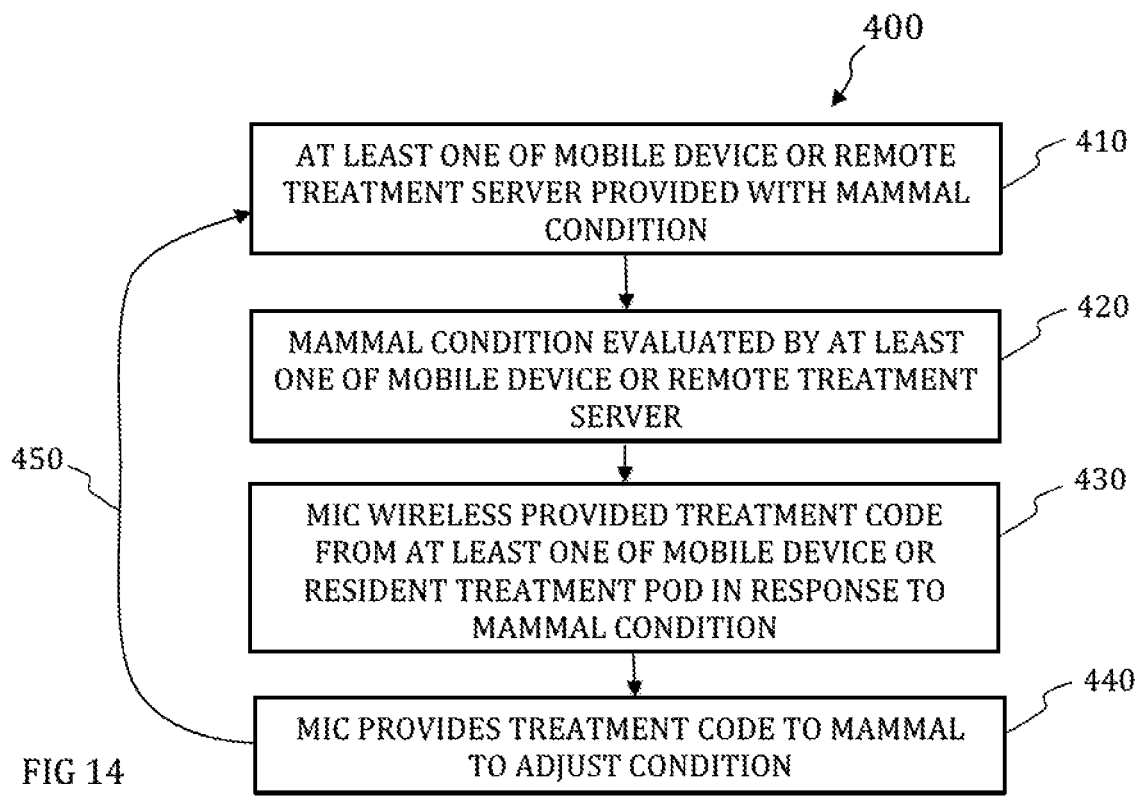

FIGS. 12-14 illustrate flow diagrams for methods of monitoring and providing neurocode based bioelectronic therapy to a mammal in accordance with the teachings of the present contained herein. Referring to FIG. 12 a block diagram 200 for a method of treatment is illustrated. Referring to block 210, a MIC monitors a mammal's condition.

Next, as shown in block 220, the mammal condition is wirelessly provided to at least one of a mobile device 100 or a remote treatment server 160 from the MIC. The MIC then wirelessly receives at least one treatment code from at least one of the mobile device 100 or remote treatment server 160 in response to the mammal condition (as monitored and reported by the MIC), as shown in block 230. Then, as shown in block 240, the MIC provides treatment code to the mammal to adjust the previously monitored and reported condition. The process can continue again as shown by feedback loop 250.

As shown in the flow diagram 300 of FIG. 13, a mobile device is provided with a mammal's condition, block 310. The condition can be provided from any combination of MIC monitoring, from measurements of vital obtained by a technician, or from external monitoring devices. Then as shown in block 320, the mammal condition is analyzed by at least one of the mobile device or a remote treatment server. It should be appreciated that some level of analysis can be provided at the mobile device, while more extensive analysis may require the computing and analysis resources of a remote treatment server. Then, as shown in block 330, a MIC is wirelessly provided a treatment code from at least one of the mobile device or a resident treatment pod in response to the analyzed mammal condition. The MIC then provides the treatment code to the mammal to adjust the mammal's condition. The treatment can be administered via the MIC, a probe via the MIC to an organ, or treatment location in the mammal.

Referring to FIG. 14, a block diagram of a treatment method 400 is illustrated. As shown in block 410, at least one of a mobile device or remote treatment server is provided with a mammal condition. As shown in block 420, the mammal condition is evaluated by at least one of the mobile device or the remote treatment server. Then as shown in block 430, the MIC is wirelessly provided a treatment code from at least one of the mobile device or the resident treatment pod in response to the analyzed mammal condition. Finally, as shown in block 440, the MIC provides the treatment code to the mammal (e.g., organ or treatment location) to adjust the condition.

The aforementioned description has thus been presented with respect to preferred and alternative embodiments of the present invention, which can be embodied in the context of a data-processing system such as computer system, in conjunction with program, and data-processing system and network depicted in FIGS. 10 and 11. The disclosed embodiments, however, are not limited to any particular application or any particular environment. Instead, those skilled in the art will find that the systems, methods and processor-readable media described herein may be advantageously applied to a variety of system and application software, including database management systems, word processors, and the like. Moreover, the systems, methods, and processor-readable media disclosed herein may be embodied on a variety of different platforms, including Macintosh. UNIX, LINUX, and the like. Therefore, the descriptions of the exemplary embodiments, which follow, are for purposes of illustration and not considered a limitation of the disclosed embodiments.

It will be understood that the circuits and other means supported by each block and combinations of blocks can be implemented by special purpose hardware, software, or firmware operating on special or general-purpose data processors, or combinations thereof. It should also be noted that, in some alternative implementations, the operations noted in the blocks might occur out of the order noted in the figures. For example, two blocks shown in succession may, in fact, be executed substantially concurrently, or the blocks may sometimes be executed in the reverse order.

The disclosed embodiments thus cover systems for monitoring mammal (animal and human) biological/health conditions, recording conditions, and providing feedback in the form of a neurocodes (e.g., bioelectronics signals, electroceutical signals, low voltage frequencies) stored in a memory and associated with a treatment based on the monitored condition. The neurocodes can be recorded, stored, and transmittable from the computer, which can be stationary or handheld, wired or wireless. Mammal biological condition can be monitored by at least one mammal implantable controller including a wireless transceiver for supporting bi-directional communication with the computer. Wireless communication can be secured by encryption between the computer and implantable controller and can utilize short-range wireless communications protocols (e.g., Bluetooth, Bluetooth LE, Near Field Communication (NFC), Radio Frequency Identification (RFID), etc.).

Computer generated analog treatment signal(s), which are aimed at the cellular nucleus, are transmitted through the plasma membrane or its ion channel pathways. Signals would travel directly through the phosphor-lipid bilayer and through the internal membrane surface so as to enter the cellular interior. The treatment signals may travel on the intermediate and/or microfilaments located in the cancer cellular interior to reach the nucleus.

The use of the hybrid scientific computer described in other issued patents of the inventor is also available to use in addition to the present invention herein described. Said neuro-electric invention records the intrinsic electrical signals found in cancer cells and then reprograms such signals. Re-transmitting such reprogrammed treatment signals can be applied anywhere in or on the human or animal body depending on the size and location of the tumor to be treated.

Methods and systems are thus disclosed for the rapid destruction of cancer tumor(s) that are made up of thousands to millions of living malignant cancer cells. This approach seeks to kill said tumor(s) by causing apoptosis or excitotoxicity and/or osmotic-shock within a human or animal for medical treatment.

Conventional targeted cancer therapies are drugs or other substances that block the growth and spread of cancer by interfering with specific molecules involved in tumor growth and spreading or engaging in metastatic colonization throughout the body. The disclosed embodiments, on the other hand, can implement a technology that kills the living cancer cells directly and quickly leaving only dead cancer cells.

The disclosed embodiments can accomplish treatment during a time from, for example, up to 20 minutes, or up to multiple hours, against a targeted cancer located in a human or animal. Eukaryote living tissue. All malignant species are eligible for such treatment. Eukaryote classification consists of cellular organisms whose individual cell contains a nucleus and other organelles enclosed within membranes. The dead tumors are removable from live patients, leaving no live cancer cells.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A bioelectronic medical system for treating a medical condition, comprising:
a mammal implanted controller (MIC) implantable within a mammal to monitor bioelectronic signals indicating a health condition of the mammal, the MIC further including a probe connectable to a target organ or a region within the mammal and associated with at least one of: a sensor, a neurocode treatment module, and a communication module;
at least one of: a mobile device and a resident treatment pod external to and associated with the mammal and adapted to communicate with the MIC;
a remote server adapted to receive recorded data representing the bioelectronics signals from the MIC over a digital data communication network from at least one of the mobile device and the resident treatment pod associated with the mammal and communicating with the MIC;
wherein the remote server evaluates the bioelectronics signals and in response provides neurocoded treatment signals to cause a change in a biological function of an organ of the mammal through at least one of the mobile device and the resident treatment pod for further transmission to the MIC, wherein a medical condition of the mammal is treated via administration of the neurocoded treatment signals to the mammal to cause the change in the biological function of the organ of the mammal by the MIC and wherein the MIC and remote server engage in ongoing analysis of the bioelectronics signals.

2. The bioelectronic medical system of claim 1, wherein the mobile device comprises:
a smartphone carried by the mammal and a neurocode treatment module, and a communications module supporting short-range data communications with the MIC and communications with the remote server via a data network to obtain periodic remote analysis and access to neurocodes for application as a medical treatment to the mammal based on the periodic remote analysis for treating the medical condition.

3. The bioelectronic medical system of claim 1, wherein the resident treatment pod comprises an electronic device associated with an environment containing the mammal and a neurocode treatment module and a communications module supporting short-range data communication with the MIC and data network communications with the remote server via a data network to obtain periodic remote analysis and access to neurocodes for application as a medical treatment to the mammal for the medical condition of the mammal based on the periodic remote analysis.

4. The bioelectronic medical system of claim 3, wherein the resident treatment pod includes an electronic device associated with an environment containing the mammal and a neurocode treatment module and a communications module supporting short-range data communication with the MIC and data network communications with the remote server via a data network to obtain periodic remote analysis and access to neurocodes for application as treatment to the mammal based on the analysis.

5. The bioelectronic medical system of claim 3, wherein the resident treatment pod is installed within at least one of: a treatment facility, a hospital or a private residence in association with a patient comprising the mammal.

6. The bioelectronic medical system of claim 3, wherein the MIC includes an electromagnetic charging module and a rechargeable power supply.

7. The bioelectronic medical system of claim 1, wherein the mobile device comprises at least one of a smartphone or tablet computer.

8. A method for providing neurocode medical treatments to a mammal, the method comprising:
obtaining realtime monitoring of a mammal condition of a mammal in the form of a bioelectronic signal by a mammal implanted controller (MIC) implanted in the mammal utilizing communications to at least one of a mobile device and a resident treatment pod provided in association with the mammal;
providing recordings of the bioelectronic signal representing realtime monitoring from the at least one of the mobile device and the resident treatment pod to a remote server via a data communications network for analysis of the mammal condition represented by the bioelectronics signal, the mammal condition comprising a medical condition of the mammal;
providing the at least one of the mobile device and the resident treatment pod with treatment updates in the form of neurocodes from the remote treatment server over the data communications network for local transmission to the MIC from the at least one of the mobile device and the resident treatment pod for application to the mammal in the form of at least one neurocode for administration to the mammal from the MIC based on the analysis by the remote server; and
providing neurocodes as treatment from the MIC as feedback in response to the realtime monitoring and remote treatment server analysis, wherein the treatment is provided to cause a change in biological function of an organ of the mammal.

9. The method of claim 8, wherein the MIC continues monitoring the mammal for condition changes and reports changes in condition to at least one of the mobile device, a resident treatment pod, and a remote treatment server when change is detected to obtain feedback treatment in the form of neurocodes.

10. A method of treating a patient having a medical condition, the method comprising:
reading a medical condition of a patient in realtime with a mammal implanted controller (MIC) implanted in the patient, wherein the MIC monitors the medical condition of the patient, the medical condition associated with an organ of a patient; and
custom delivering individualized bioelectric therapy comprising at least one bioelectric signal to the patient and/or the organ of the patient in response to the reading,
wherein the bioelectric therapy acts to cause a change in a biological function of the organ of the patient.

11. The method of claim 10, wherein the individualized bioelectric therapy is delivered to the patient and/or organ by a device comprising:
a probe for determining a resident electrical signal found in the organ;
a computer system comprising a processor for modifying each determined resident electrical signal to form at least one electrical signal unique to each determined resident electrical signal, and
data storage for storing all bioelectronic signals; and
a probe for applying a bioelectronic signal to the organ for the bioelectronic therapy.

* * * * *